(12) United States Patent (10) Patent No.: US 12,303,314 B2
Taki (45) Date of Patent: May 20, 2025

(54) IMAGE PROCESSING APPARATUS, IMAGE PROCESSING METHOD, AND IMAGE PROCESSING PROGRAM

(71) Applicant: FUJIFILM Corporation, Tokyo (JP)

(72) Inventor: Tomoko Taki, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 684 days.

(21) Appl. No.: 17/079,118

(22) Filed: Oct. 23, 2020

(65) Prior Publication Data

US 2021/0128094 A1 May 6, 2021

(30) Foreign Application Priority Data

Oct. 31, 2019 (JP) .................................. 2019-199067

(51) Int. Cl.
*A61B 6/50* (2024.01)
*A61B 6/00* (2024.01)
*A61B 6/46* (2024.01)

(52) U.S. Cl.
CPC .............. *A61B 6/505* (2013.01); *A61B 6/461* (2013.01); *A61B 6/482* (2013.01); *A61B 6/5217* (2013.01); *A61B 6/5229* (2013.01)

(58) Field of Classification Search
CPC ......... A61B 6/505; A61B 6/461; A61B 6/482; A61B 6/5258; A61B 6/5282;
(Continued)

(56) References Cited

U.S. PATENT DOCUMENTS 8,290,564 B2 * 10/2012 Lang ..................... G06T 7/0012
600/407
2008/0119719 A1 * 5/2008 Ascenzi ................ G06T 7/0012
600/410
(Continued)

FOREIGN PATENT DOCUMENTS

JP H10-155115 A 6/1998
JP 2003-230557 A 8/2003
(Continued)

OTHER PUBLICATIONS

Kumasaka, S., Kiyohara, S., Takahashi, T. et al. Morphologically extracted trabecular skeleton superimposed upon digital radiograph structure. J Bone Miner Metab 18, 208-211 (2000). https://doi.org/10.1007/s007740070021 (Year: 2000).*

*Primary Examiner* — Pascal M Bui Pho
*Assistant Examiner* — Michael Yiming Fang
(74) *Attorney, Agent, or Firm* — Studebaker Brackett PLLC

(57) ABSTRACT

An image processing apparatus includes a first acquisition unit, a derivation unit, a second acquisition unit, and a trabecula image generation unit. The first acquisition unit acquires a first radiographic image and a second radiographic image by simple imaging of a subject including a bone tissue. The derivation unit derives a bone mass in a bone part region of the subject based on the first radiographic image and the second radiographic image. The second acquisition unit acquires a medical image that represents a state of a trabecula and is different from the first radiographic image and the second radiographic image. The trabecula image generation unit applies the medical image to the bone part region of the first radiographic image based on the bone mass derived by the derivation unit to generate a trabecula image representing a trabecula of the bone tissue.

19 Claims, 10 Drawing Sheets

(58) Field of Classification Search
CPC ... A61B 6/4266; A61B 6/5217; A61B 6/5235; A61B 6/00; A61B 6/52; G06T 7/00; G06T 3/4038
See application file for complete search history.

(56) References Cited

U.S. PATENT DOCUMENTS

| | | | |
|---|---|---|---|
| 2011/0305405 A1 | 12/2011 | Kawamura | |
| 2015/0221080 A1* | 8/2015 | Yamamoto | A61B 6/505 378/4 |
| 2015/0348259 A1* | 12/2015 | Souza | A61B 6/466 382/131 |
| 2018/0028139 A1* | 2/2018 | Kuwabara | A61B 6/4291 |
| 2018/0122094 A1 | 5/2018 | Naito | |
| 2020/0337782 A1* | 10/2020 | Glassman | A61B 90/37 |
| 2022/0249202 A1* | 8/2022 | Choi | A61B 6/032 |

FOREIGN PATENT DOCUMENTS

| | | |
|---|---|---|
| JP | 2011-255060 A | 12/2011 |
| JP | 2015-043959 A | 3/2015 |

\* cited by examiner

IMAGE PROCESSING APPARATUS, IMAGE PROCESSING METHOD, AND IMAGE PROCESSING PROGRAM

CROSS-REFERENCE TO RELATED APPLICATION

This application claims priority from Japanese Patent Application No. 2019-199067, filed on Oct. 31, 2019, the disclosure of which is incorporated by reference herein in its entirety.

BACKGROUND

Field of the Invention

A technique of the present disclosure relates to an image processing apparatus, an image processing method, and an image processing program.

Related Art

There is known a technique that acquires information relating to a trabecula of a bone of a subject from a medical image. For example, JP2003-230557A describes a technique that extracts a skeleton component of a trabecula with a morphological filter for a medical image of a bone, calculates a parameter of a skeleton structure using bone morphometry for the extracted skeleton component, and outputs the calculated parameter.

Furthermore, for example, JP1998-155115 A (JP-H10-155115A) describes a technique that executes highlighting processing of a trabecula for a bone part image, in which an image of a bone tissue obtained through energy subtraction processing is extracted or highlighted, thereby acquiring form information of the trabecula.

Incidentally, it is known that, in a case where a bone mass decreases due to aging or the like, a bone disease, such as osteoporosis or compression fracture, is highly likely to occur, it is important to make a subject become aware of the decreased state of the bone mass in prevention or treatment of the bone disease. While the decrease in bone mass is reflected in a state of the trabecula, in a state of the trabecula obtained by the technique in the related art, the subject may hardly recognize (become aware of) the decreased state of the bone mass, and it is desirable to provide a trabecula image for making the subject become easily aware of the decreased state of the bone mass.

SUMMARY

The present disclosure has been accomplished in view of the above circumstances, and an object of the present disclosure is to provide an image processing apparatus, an image processing method, and an image processing program capable of generating a trabecula image for enabling easy awareness of a decreased state of a bone mass of a subject.

In order to achieve the above-described object, a first aspect of the present disclosure provides an image processing apparatus comprising a first acquisition unit that acquires a radiographic image obtained by simple imaging of a subject including a bone tissue, a derivation unit that derives a bone mass in a bone part region of the subject based on the radiographic image, a second acquisition unit that acquires a medical image, which represents a state of a trabecula and is different from the radiographic image, and a trabecula image generation unit that applies the medical image to the bone part region of the radiographic image based on the bone mass derived by the derivation unit to generate a trabecula image representing a trabecula of the bone tissue.

According to a second aspect of the present disclosure, in the image processing apparatus according to the first aspect of the present disclosure, the medical image is a medical image captured by an imaging apparatus for imaging a state of a trabecula of a bone.

According to a third aspect of the present disclosure, in the image processing apparatus according to the first aspect or the second aspect of the present disclosure, the trabecula image generation unit pastes the medical image to the bone part region of the radiographic image to generate the trabecula image representing the trabecula of the bone tissue.

According to a fourth aspect of the present disclosure, in the image processing apparatus according to the third aspect of the present disclosure, the derivation unit derives a bone mass of each of a plurality of regions obtained by dividing the bone part region, and the trabecula image generation unit pastes the medical image to each of the plurality of regions to generate the trabecula image.

According to a fifth aspect of the present disclosure, in the image processing apparatus according to the third aspect of the present disclosure, the derivation unit derives a bone mass for each pixel of the bone part region, and the trabecula image generation unit pastes the medical image to each pixel of the bone part region to generate the trabecula image.

According to a sixth aspect of the present disclosure, the image processing apparatus according to any one aspect of the first aspect to the fifth aspect further comprises a distribution diagram generation unit that generates a distribution diagram of the bone mass in the bone part region based on the bone mass derived by the derivation unit, and the trabecula image generation unit generates the trabecula image based on the distribution diagram.

According to a seventh aspect of the present disclosure, in the image processing apparatus according to any one aspect of the first aspect to the sixth aspect of the present disclosure, the first acquisition unit acquires a first radiographic image and a second radiographic image acquired by radiation having different energy distributions transmitted through the subject as the radiographic image. The image processing apparatus further comprises a bone part image generation unit that generates a bone part image representing a bone part region with a bone tissue of the subject from the first radiographic image and the second radiographic image. The derivation unit derives a bone mass based on the bone part image, and the trabecula image generation unit applies the medical image to the bone part region of any one of the first radiographic image, the second radiographic image, and the bone part image to generate the trabecula image.

According to an eighth aspect of the present disclosure, the image processing apparatus according to any one aspect of the first aspect to the seventh aspect of the present disclosure further comprises a display controller that makes a display unit display an image in a case where a health problem occurs in the bone mass derived by the derivation unit or a bone mass smaller than the derived bone mass by a predetermined mass.

Furthermore, in order to achieve the above-described object, a ninth aspect of the present disclosure provides an image processing method comprising acquiring a radiographic image obtained by simple imaging of a subject including a bone tissue, deriving a bone mass in a bone part region of the subject based on the radiographic image, acquiring a medical image, which represents a state of a trabecula and is different from the radiographic image, and applying the medical image to the bone part region of the radiographic image based on the bone mass derived by the derivation unit to generate a trabecula image representing a trabecula of the bone tissue.

Furthermore, in order to achieve the above-described object, a tenth aspect of the present disclosure provides an image processing program that causes a computer to execute acquiring a radiographic image obtained by simple imaging of a subject including a bone tissue, deriving a bone mass in a bone part region of the subject based on the radiographic image, acquiring a medical image, which represents a state of a trabecula and is different from the radiographic image, and applying the medical image to the bone part region of the radiographic image based on the bone mass derived by the derivation unit to generate a trabecula image representing a trabecula of the bone tissue.

According to the present disclosure, it is possible to easily generate a trabecula image for enabling easy awareness of a decreased state of a bone mass of subject.

DETAILED DESCRIPTION

Figure 1:
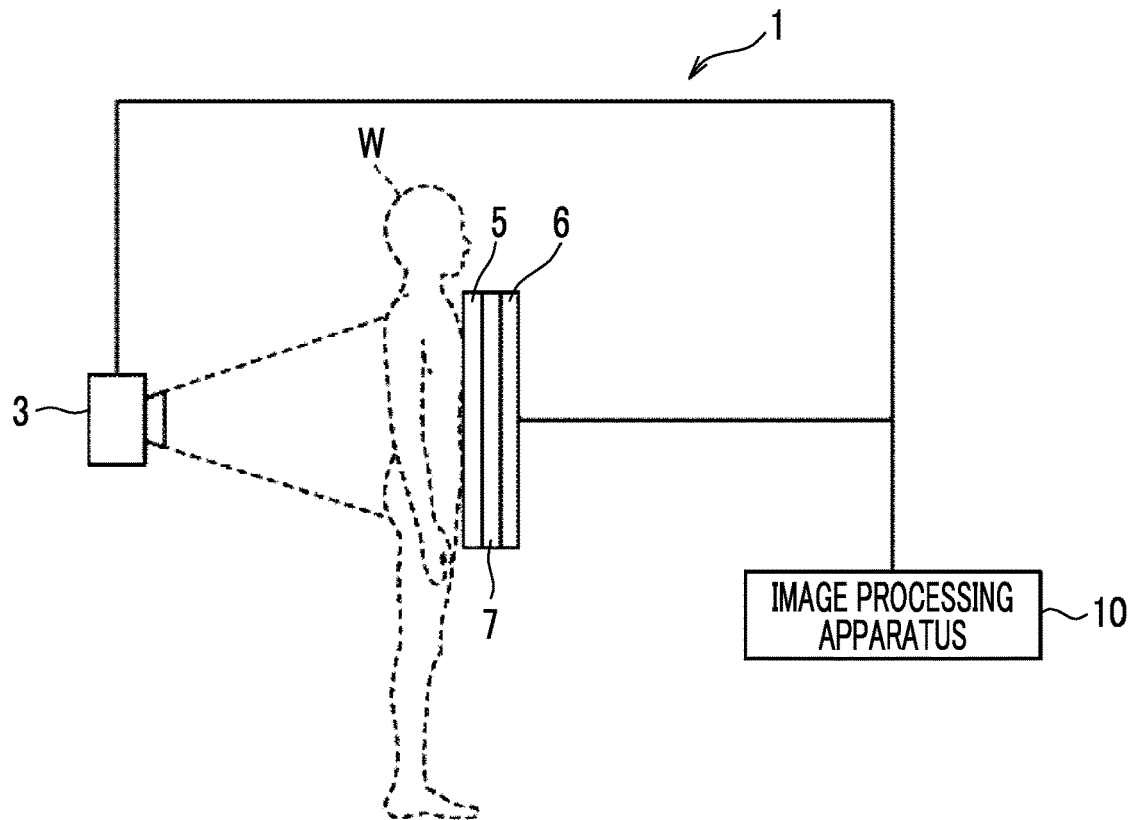
FIG. 1 is a schematic block diagram showing an example of the configuration of a radiography system of a first embodiment.

Hereinafter, examples of an embodiment for implementing the technique of the present disclosure will be described in detail referring to the drawings. In the drawings, the substantially same or equivalent components or portions are represented by the same reference numerals.

FIG. 1 is a schematic block diagram showing an example of the configuration of a radiography system 1 of the embodiment. The radiography system 1 comprises a radiation source 3, a first radiation detector 5, a second radiation detector 6, a radiation-energy conversion filter 7, and an image processing apparatus 10.

Each of the first radiation detector 5 and the second radiation detector 6 generates a radiographic image based on radiation emitted from the radiation source 3 and transmitted through a subject W. Each of the first radiation detector 5 and the second radiation detector 6 may have a form of a so-called flat panel detector (FPD) in which a radiographic image signal is read by turning on and off a thin film transistor (TFT) switch. In this case, each of the first radiation detector 5 and the second radiation detector 6 may be a direct radiation detector that is directly irradiated with radiation to generate an electric charge or an indirect radiation detector that converts radiation into visible light once and converts the visible light into an electric charge signal. Each of the first radiation detector 5 and the second radiation detector 6 may be a radiation detector to which a Computed Radiography (CR) technique for reading an image recorded on an imaging plate through irradiation of a laser beam is applied. The radiation-energy conversion filter 7 is configured of a metal plate, such as a copper plate, capable of absorbing a specific energy component included in radiation.

A radiographic image is captured in a state in which the first radiation detector 5, the radiation-energy conversion filter 7, and the second radiation detector 6 are superimposed in this order from a side close to the radiation source 3 (subject W), whereby one-shot energy subtraction is realized. That is, with irradiation with radiation from the radiation source 3 once, two radiographic images having different energy distributions are acquired from the first radiation detector 5 and the second radiation detector 6.

In the first radiation detector 5, a first radiographic image G1 of the subject W according to low-energy radiation including so-called soft rays is acquired. Furthermore, in the second radiation detector 6, a second radiographic image G2 of the subject W according to high-energy radiation without soft rays is acquired. Each of the first radiographic image G1 and the second radiographic image G2 is input to the image processing apparatus 10.

In the radiography system 1 of the embodiment, in a case where the subject W is imaged, a scattered ray elimination grid that eliminates scattered ray components of radiation transmitted through the subject W is not used. For this reason, primary ray components and scattered ray components of radiation transmitted through the subject W are included in each of the first radiographic image G1 and the second radiographic image G2.

The image processing apparatus 10 has a function of generating a trabecula image according to a bone mass of a bone tissue of the subject W based on the first radiographic image G1 and the second radiographic image G2 acquired on the subject W.

Figure 2:
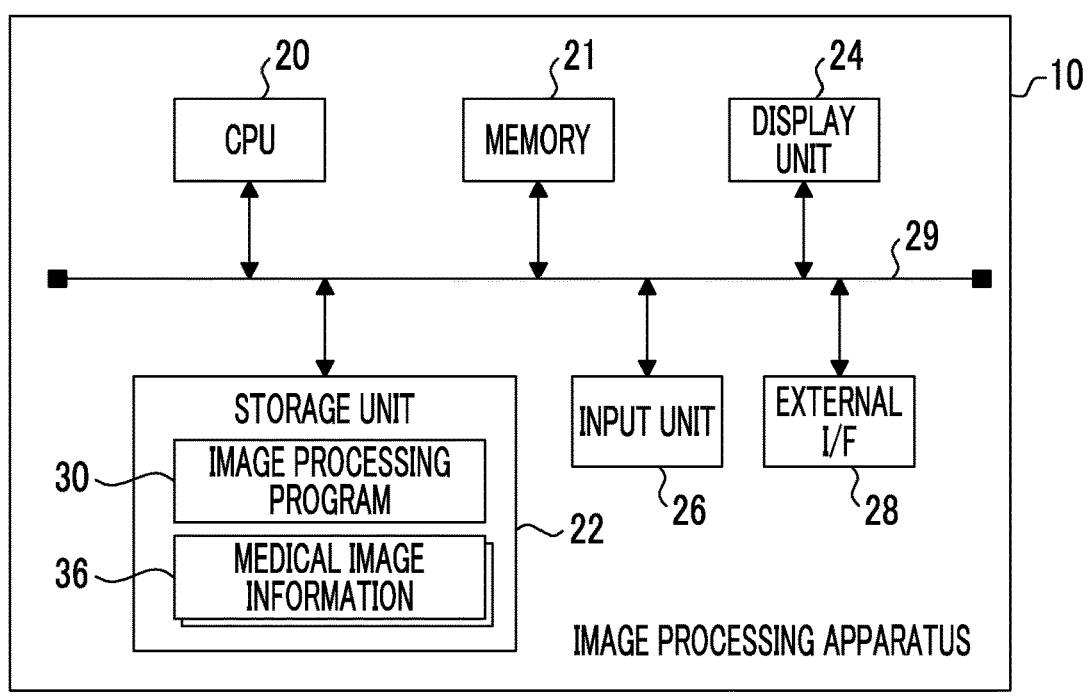
FIG. 2 is a diagram showing an example of the hardware configuration of an image processing apparatus of the first embodiment.

FIG. 2 is a diagram showing an example of the hardware configuration of the image processing apparatus 10 of the embodiment. The image processing apparatus 10 comprises a central processing unit (CPU) 20, a memory 21, a storage unit 22, a display unit 24, such as a liquid crystal display, an input unit 26, such as a keyboard and a mouse, and an external interface (I/F) 28. The CPU 20, the memory 21, the storage unit 22, the display unit 24, the input unit 26, and the external I/F 28 are connected to a bus 29. The first radiation detector 5 and the second radiation detector 6 are connected to the external I/F 28. The image processing apparatus 10 may configure, for example, a personal computer or a server computer.

The storage unit 22 is realized by a hard disk drive (HDD), a solid state drive (SSD), a flash memory, or the like. An image processing program 30 is stored in the storage unit 22 as a storage medium. The CPU 20 reads the image processing program 30 from the storage unit 22, then, develops the image processing program 30 to the memory 21, and executes the developed image processing program 30. Furthermore, medical image information 36 described below is also stored in the storage unit 22.

Figure 3:
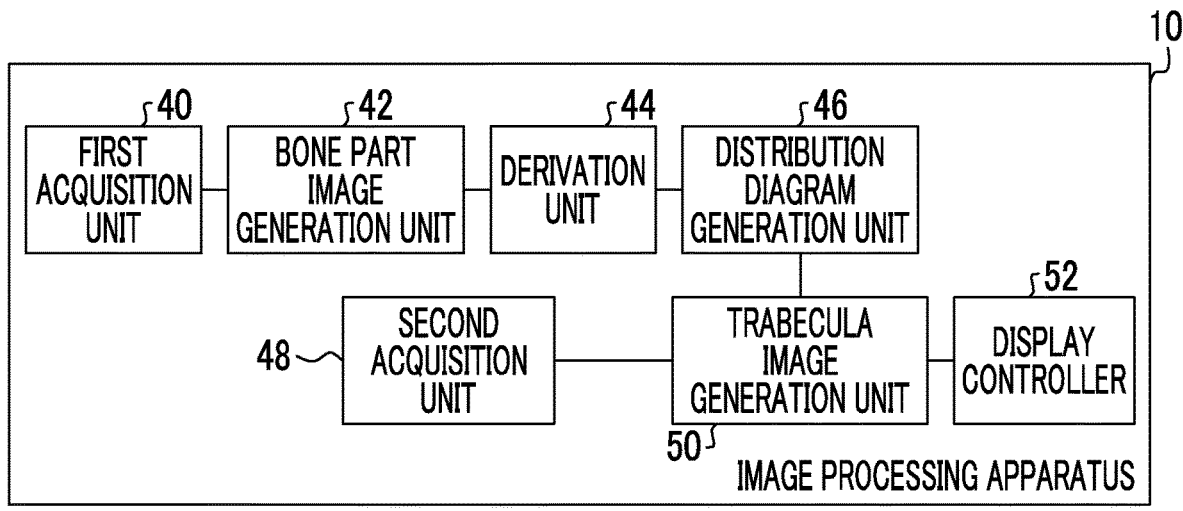
FIG. 3 is a functional block diagram showing an example of the functional configuration of the image processing apparatus of the first embodiment.

FIG. 3 is a functional block diagram showing an example of the functional configuration of the image processing apparatus 10. The image processing apparatus 10 comprises a first acquisition unit 40, a bone part image generation unit 42, derivation unit 44, a distribution diagram generation unit 46, a second acquisition unit 48, a trabecula image generation unit 50, and a display controller 52. The image processing apparatus 10 functions as the first acquisition unit 40, the bone part image generation unit 42, the derivation unit 44, the distribution diagram generation unit 46, the second acquisition unit 48, the trabecula image generation unit 50, and the display controller 52 by the CPU 20 executing the image processing program 30.

The first acquisition unit 40 acquires the first radiographic image G1 and the second radiographic image G2 acquired by radiation having different energy distributions transmitted through the subject W. Specifically, the first acquisition unit 40 acquires image data representing the first radiographic image G1 output from the first radiation detector 5, and acquires image data representing the second radiographic image G2 output from the second radiation detector 6. In imaging of the first radiographic image G1 and the second radiographic image G2, imaging conditions, such as an irradiation dose, a tube voltage, and a source-to-image receptor distance (SID) of radiation from the radiation source 3, are set. The set imaging conditions are stored in the storage unit 22 in association with each of the first radiographic image G1 and the second radiographic image G2. The SID used herein represents a distance between the radiation source 3 and a detection surface of radiation in the first radiation detector 5 in a case of the first radiation detector 5, and represents a distance between the radiation source 3 and a detection surface of radiation in the second radiation detector 6 in a case of the second radiation detector 6. The first acquisition unit 40 of the embodiment corresponds to an example of a first acquisition unit and an acquisition unit of the present disclosure.

Figure 4:
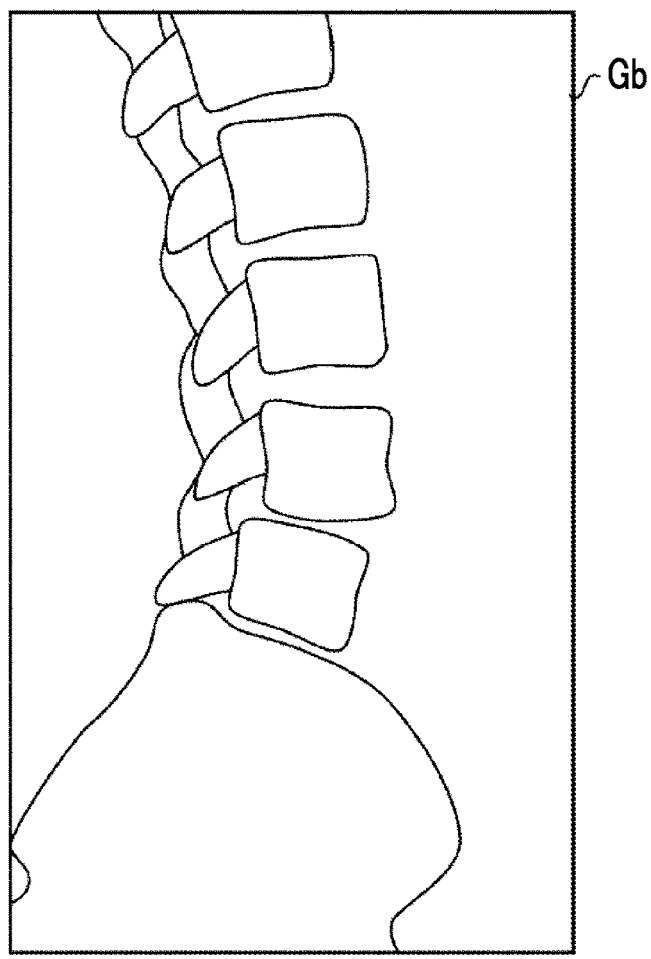
FIG. 4 is a diagram showing an example of a bone part image that is generated by a bone part image generation unit of the first embodiment.

The bone part image generation unit 42 generates a bone part image Gb representing a bone part region with a bone tissue of the subject W from the first radiographic image G1 and the second radiographic image G2 acquired by the first acquisition unit 40. FIG. 4 shows an example of a bone part image Gb generated by the bone part image generation unit 42. The bone part image Gb shown in FIG. 4 is a bone part image Gb generated by a first radiographic image G1 and a second radiographic image G2 obtained by performing simple imaging for a bone tissue including first to fifth lumbar vertebrae of the subject W. In general, a lumbar vertebra or a thighbone is used in measurement of a bone mass or a bone mineral content.

As an example, the bone part image generation unit 42 of the embodiment performs weighting subtraction between corresponding pixels as shown in Expression (1) described below for the first radiographic image G1 and the second radiographic image G2, thereby generating the bone part image Gb in which only a bone tissue of the subject W included in the first radiographic image G1 and the second radiographic image G2 is extracted. In Expression (1) described below, $\mu b$ is a weighting factor, and x and y are coordinates of each pixel of the bone part image Gb.

$$Gb(x,y)=G1(x,y)-\mu b \times G2(x,y) \qquad (1)$$

As described above, scattered ray components other than primary ray components of radiation transmitted through the subject W are included in each of the first radiographic image G1 and the second radiographic image G2. For this reason, it is preferable that the scattered ray components are eliminated from the first radiographic image G1, the second radiographic image G2, and the bone part image Gb. Information for eliminating the scattered ray components from the first radiographic image G1, the second radiographic image G2, and the bone part image Gb is not particularly limited. For example, the bone part image generation unit 42 may apply the method described in JP2015-043959A to eliminate the scattered ray components from the first radiographic image G1, the second radiographic image G2, and the bone part image Gb.

For example, a method in which a plurality of pieces of data for scattered ray correction obtained in advance by calibration using a phantom simulating a human body and a flat plate-shaped radiation shielding member with a pinhole, through which radiation is transmitted, in a center portion is stored in the storage unit 22, and the bone part image generation unit 42 eliminates scattered rays from the first radiographic image G1, the second radiographic image G2, and the bone part image Gb using the data for scattered ray correction may be applied. The amount of scattered rays to be generated is different depending on the above-described imaging conditions or conditions, such as a body thickness of the subject W and a composition (a ratio of muscle and fat) of the soft tissue of the subject. For this reason, it is preferable that the data for scattered ray correction is acquired in advance according to each condition using a plurality of kinds of phantoms according to various conditions.

A distance (SID) between the radiation source 3 and each of the first radiation detector 5 and the second radiation detector 6, or the like is different. For this reason, a spread of scattered rays, called a point spread function (PSF), or intensity of scattered rays is different and a content of scattered rays is different between the first radiographic image G1 and the second radiographic image G2. For this reason, the data for scattered ray correction may be stored in association with each of the first radiographic image G1 and the second radiographic image G2 or processing of correcting a difference in scattered ray content between the first radiographic image G1 and the second radiographic image G2 may be executed.

As described above, since the amount of scattered ray components included in each of the first radiographic image G1 and the second radiographic image G2 is different according to the body thickness of the subject W, it is preferable that the bone part image generation unit 42 eliminates scattered rays in consideration of the body thickness of the subject W.

A method in which the bone part image generation unit 42 derives the body thickness of the subject W is not particularly limited, and a body thickness distribution T(x,y) of the subject W may be derived, for example, using a method described in JP2015-043959A. In the following description, an example of a method of deriving the body thickness distribution T(x,y) of the subject W will be described. In the example, although a form using the first radiographic image G1 acquired by the radiation detector 5 on the side close to the subject W will be described, the present disclosure is not limited to this form, and the second radiographic image G2 may be used.

First, the bone part image generation unit 42 acquires a virtual model K of the subject W having an initial body thickness distribution T0(x,y). The virtual model K is data that virtually represents the subject W and has the body thickness compliant with the initial body thickness distribution T0(x,y) in association with a coordinate position of each pixel of the first radiographic image G1. The virtual model K of the subject W having the initial body thickness distribution T0(x,y) may be stored in advance in the storage unit 22.

Next, the bone part image generation unit 42 generates an image, in which an estimated primary ray image of a primary ray image to be obtained by imaging the virtual model K and an estimated scattered ray image of a scattered ray image to be obtained by imaging the virtual model K are composed, as an estimated image of the first radiographic image G1 obtained by imaging the subject W based on the virtual model K.

Next, the bone part image generation unit 42 corrects the initial body thickness distribution T0(x,y) of the virtual model K such that a difference between the estimated image and the first radiographic image G1 becomes small. The bone part image generation unit 42 repeats the generation of the estimated image and the correction of the body thickness distribution until the difference between the estimated image and the first radiographic image G1 satisfies a predetermined end condition. The bone part image generation unit 42 derives, as the body thickness distribution T(x,y) of the subject W, the body thickness distribution in a case where the end condition is satisfied.

The derivation unit 44 derives the bone mass in the bone part region of the subject W based on the bone part image Gb generated by the bone part image generation unit 42. As an example, the derivation unit 44 of the embodiment derives a bone mass B for each pixel of the bone part image Gb. A form may be made in which the bone mass B may be derived on all bones included in the bone part image Gb or the bone mass B may be derived only on a predetermined bone. As an example, in the embodiment, in regard to the bone part image Gb, a predetermined bone is set to first to fifth lumbar vertebrae, and the derivation unit 44 derives a bone mass B for each pixel of a bone part region corresponding to the first to fifth lumbar vertebrae and does not derive a bone mass B on a bone part region corresponding to other bones included in the bone part image Gb. Hereinafter, the bone part region on which the derivation unit 44 derives the bone mass B refers to the bone part region corresponding to the first to fifth lumbar vertebrae.

Specifically, the derivation unit 44 derives the bone mass B corresponding to each pixel by converting each pixel value of the bone part region of the bone part image Gb into a pixel value of a bone image in a case of being acquired under a reference imaging condition. More specifically, the derivation unit 44 derives the bone mass B of each pixel by correcting each pixel value of the bone part image Gb using a correction coefficient acquired from a look-up table (not shown) described below.

Here, as the tube voltage in the radiation source 3 is higher and radiation emitted from the radiation source 3 has higher energy, contrast of a soft tissue and a bone tissue in a radiographic image becomes smaller. Furthermore, in a process in which radiation is transmitted through the subject W, a low-energy component of radiation is absorbed by the subject W, and beam hardening that radiation increases in energy occurs. The increase in energy of radiation due to beam hardening becomes greater as the body thickness of the subject W is greater.

Figure 5:
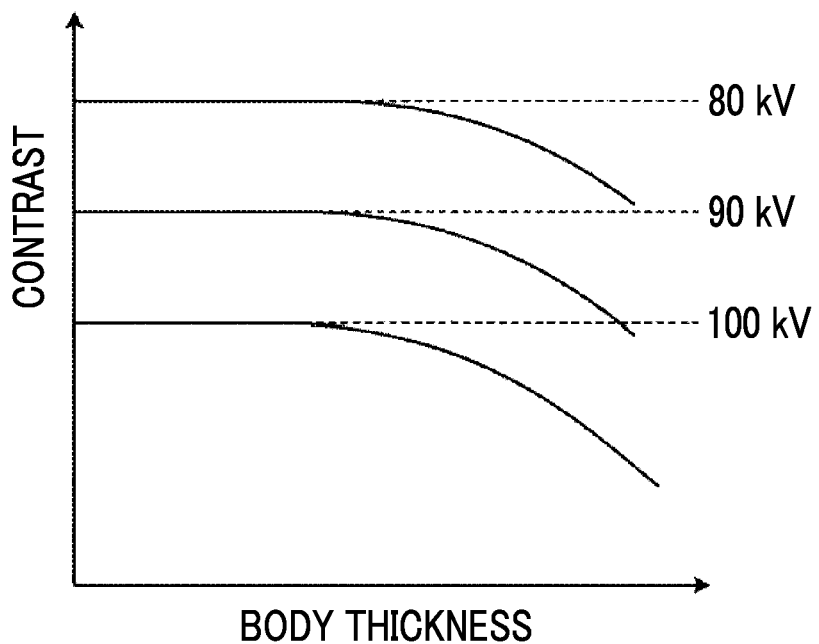
FIG. 5 is a diagram showing an example of a relationship between a body thickness of a subject and contrast of a bone tissue and a soft tissue.

FIG. 5 is a diagram showing a relationship between the body thickness of the subject W and contrast of a bone tissue and a soft tissue. FIG. 5 shows a relationship between the body thickness of the subject W and the contrast of the bone part and the soft tissue at three tube voltages of 80 kV, 90 kV, and 100 kV. As shown in FIG. 5, the contrast becomes lower as the tube voltage is higher. In a case where the body thickness of the subject W exceeds a certain value, the contrast becomes lower as the body thickness is greater. As a pixel value of a bone part region in the bone part image Gb is greater, the contrast of the bone tissue and the soft tissue becomes higher. For this reason, the relationship shown in FIG. 5 is shifted to a higher contrast side as the pixel value of the bone part region in the bone part image Gb is greater.

In the embodiment, the look-up table (not shown) for acquiring the correction coefficient for correcting a difference in contrast according to the tube voltage at the time of imaging and a decrease in contrast due to the influence of beam hardening in the bone part image Gb is stored in the storage unit 22. The correction coefficient is a coefficient for correcting each pixel value of the bone part image Gb.

Figure 6:
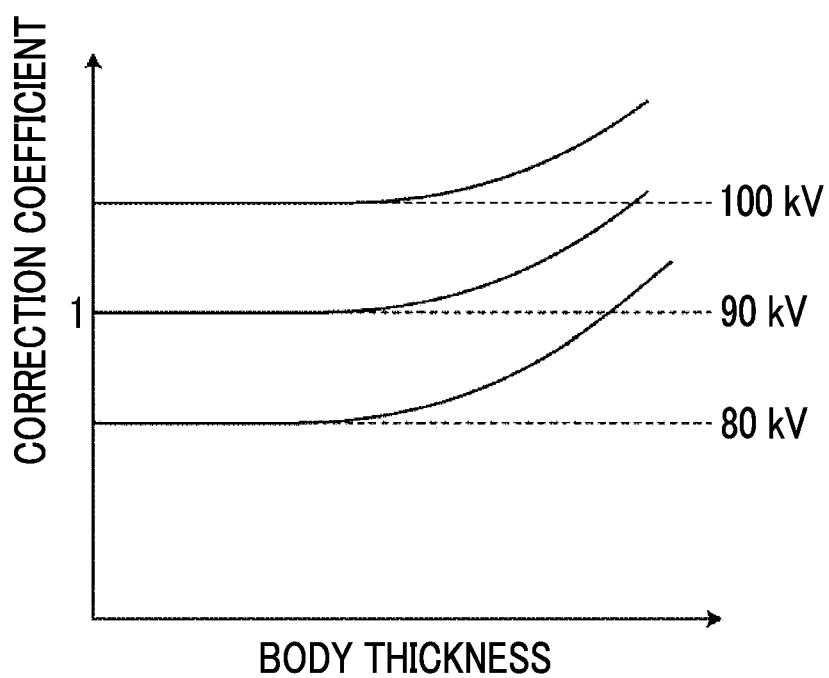
FIG. 6 is a diagram showing an example of a look-up table that is used in the first embodiment.

FIG. 6 is a diagram showing an example of the look-up table stored in the storage unit 22. In FIG. 6, a look-up table in which a reference imaging condition of a tube voltage 90 kV is set is illustrated. As shown in FIG. 6, in the look-up table, as the tube voltage is greater, and as the body thickness of the subject is greater, a greater correction coefficient is set. In the example shown in FIG. 6, since the reference imaging condition is the tube voltage 90 kV, in a case where the tube voltage is 90 kV and the body thickness is 0, the correction coefficient is 1. In FIG. 6, although the look-up table is shown in a two-dimensional manner, the correction coefficient is different according to the pixel value of the bone part region. For this reason, the look-up table actually becomes a three-dimensional table in which an axis representing the pixel value of the bone part region is added.

The derivation unit 44 extracts the body thickness distribution T(x,y) of the subject W and a correction coefficient C0(x,y) of each pixel according to imaging conditions including a set value of the tube voltage stored in the storage unit 22 from the look-up table. Then, as shown in Expression (2) described below, the derivation unit 44 derives a bone mass B(x,y) of each pixel of the bone part image Gb by multiplying each pixel (x,y) of the bone part region in the bone part image Gb by the correction coefficient C0(x,y). The bone mass B(x,y) derived in this way represents a pixel value of a bone part region included in a radiographic image that is acquired by imaging the subject W at the tube voltage of 90 kV as the reference imaging condition, and from which the influence of beam hardening is eliminated.

$$B(x,y)=C0(x,y) \times Gb(x,y) \quad (2)$$

Figure 7:
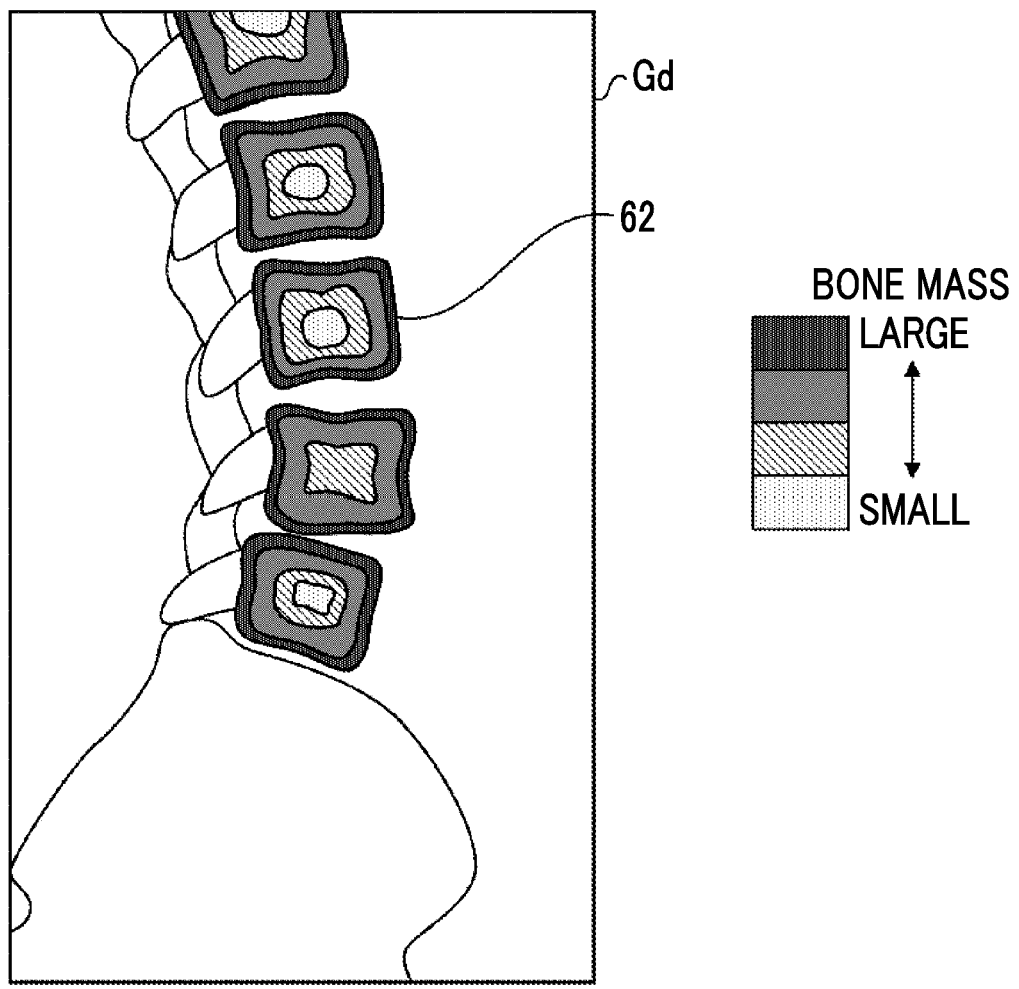
FIG. 7 is a diagram showing an example of a distribution diagram that is generated by a distribution diagram generation unit of the first embodiment.

The distribution diagram generation unit 46 generates a distribution diagram of the bone mass in the bone part region of the subject W, specifically, a two-dimensional distribution diagram based on the bone mass B derived by the derivation unit 44. FIG. 7 shows an example of a two-dimensional distribution diagram Gd generated by the distribution diagram generation unit 46. The two-dimensional distribution diagram Gd shown in FIG. 7 represents a two-dimensional distribution of the bone mass B on the first to fifth lumbar vertebrae of the subject W. In the two-dimensional distribution diagram Gd shown in FIG. 7, a two-dimensional distribution diagram in which the bone mass B is divided into four stages according to the value of the bone mass B and different colors are mapped according to the stages. In FIG. 7, a distribution state of the stage of the bone mass B is indicated by a difference in hatching.

The distribution diagram generation unit 46 generates the bone part image Gb by discriminating to which of the four stages the bone mass B corresponds for each pixel of the bone part region and specifying a color associated with the discriminated stage as a color corresponding to the pixel.

The second acquisition unit 48 acquires medical image information 36 that represents a state of a trabecula and represents a medical image different from the first radiographic image G1 and the second radiographic image G2 acquired by the first acquisition unit 40. In the image processing apparatus 10 of the embodiment, the medical image information 36 of each of a plurality of medical images according to bone masses is stored in the storage unit 22, and the second acquisition unit 48 acquires the medical image information 36 representing the medical image according to the bone mass B from the storage unit 22.

Figure 8A:
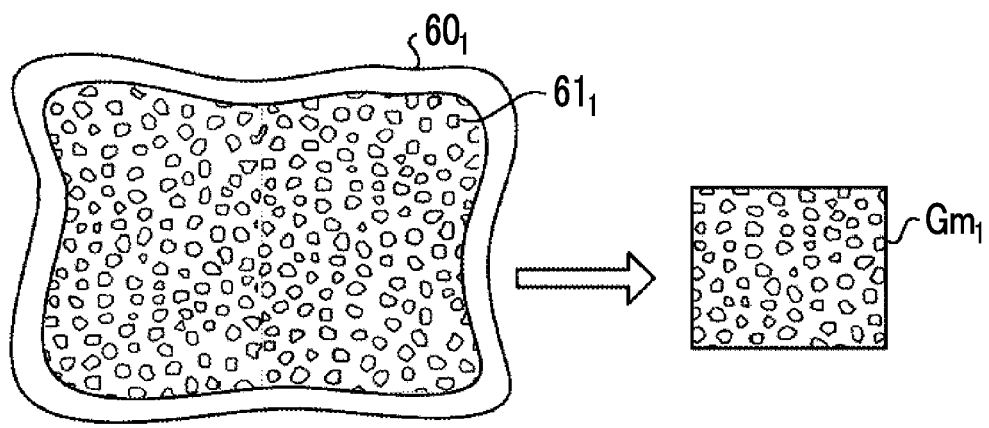
FIG. 8A is a diagram showing an example of a medical image with a bone having a certain bone mass.
Figure 8B:
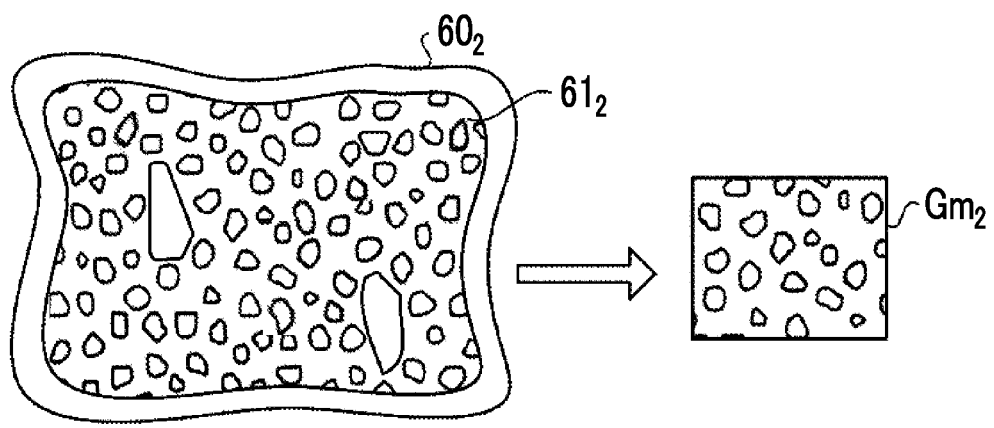
FIG. 8B is a diagram showing an example of a medical image with a bone having a bone mass smaller than the bone in the medical image shown in FIG. 8A.

An example of a medical image that is represented by the medical image information 36 stored in the storage unit 22 is shown in FIGS. 8A and 8B. FIG. 8A shows an example of a medical image $Gm_1$ obtained from a cross-sectional image of a bone $60_1$ that has a certain bone mass and includes a trabecula $61_1$. FIG. 8B shows an example of a medical image $Gm_2$ obtained from a cross-sectional image of a bone $60_2$ that has a bone mass smaller than the bone $60_1$ and includes a trabecula $61_2$.

As shown in the medical images $Gm_1$ and $Gm_2$, in the embodiment, an image of only a portion of a trabecula is used as a medical image. Furthermore, in the embodiment, a medical image captured by an imaging apparatus for imaging a state of a trabecula of a bone is used as a medical image. As the medical image, for example, a micro (μ) Computed Tomography (CT) image, a Magnetic Resonance Imaging (MRI) image, an image obtained by tomosynthesis imaging, and the like are exemplified. Alternatively, for example, an optical photographic image obtained by imaging of a cross section of a bone may be used as a medical image. In addition, for example, an image generated by Computer Graphics (CG) may be used as a medical image. A bone that is targeted for imaging of a medical image may not be a bone of the subject W. Alternatively, a bone that is targeted for imaging of the medical image and a bone that is targeted for imaging of the bone part image Gb may be different in type.

The trabecula image generation unit 50 pastes the medical image acquired by the second acquisition unit 48 to the bone part region of the first radiographic image G1 acquired by the first acquisition unit 40 based on the two-dimensional distribution diagram Gd generated by the distribution diagram generation unit 46 according to the bone mass B derived by the derivation unit 44, thereby generating a trabecula image representing the trabecula of the bone tissue. In the embodiment, "pasting" the medical image is not limited to superimposing the medical image on the bone part region, and also includes replacing the radiographic image of the bone part region with the medical image.

Figure 9:
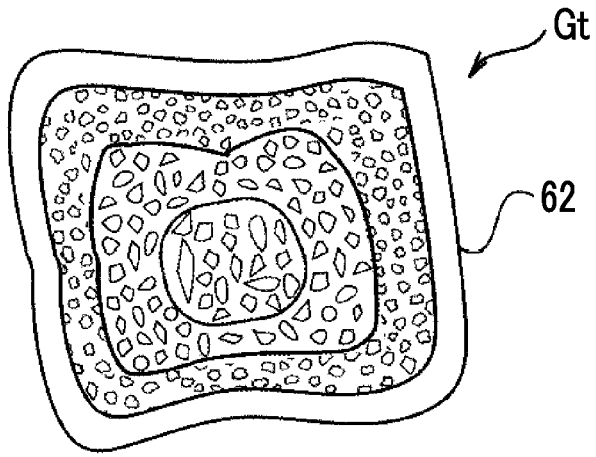
FIG. 9 is a diagram showing an example of a trabecula image that is generated by a trabecula image generation unit of the first embodiment.

Specifically, for each region (hereinafter, referred to as a "stage region") divided according to the stages of the bone mass B, the trabecula image generation unit 50 of the embodiment derives an average value of the bone masses B of the respective regions based on the two-dimensional distribution diagram Gd. In addition, the trabecula image generation unit 50 makes the second acquisition unit 48 acquire the medical image information 36 representing the medical image corresponding to the bone mass B as the derived average value for each stage region. Furthermore, the trabecula image generation unit 50 pastes the medical image, which is represented by the medical image information 36 acquired by the second acquisition unit 48, to each stage region in the bone part region of the first radiographic image G1 to generate a trabecula image. FIG. 9 shows an example of a trabecula image Gt generated by the trabecula image generation unit 50. In FIG. 9, for simplification, only the trabecula image Gt corresponding to a third lumbar vertebra 62 (also see FIG. 7) is shown. In this way, the trabecula image Gt is composed of the medical image representing the trabecula according to the bone mass B.

The display controller 52 performs control that the display unit 24 displays the trabecula image Gt generated by the trabecula image generation unit 50.

Figure 10:
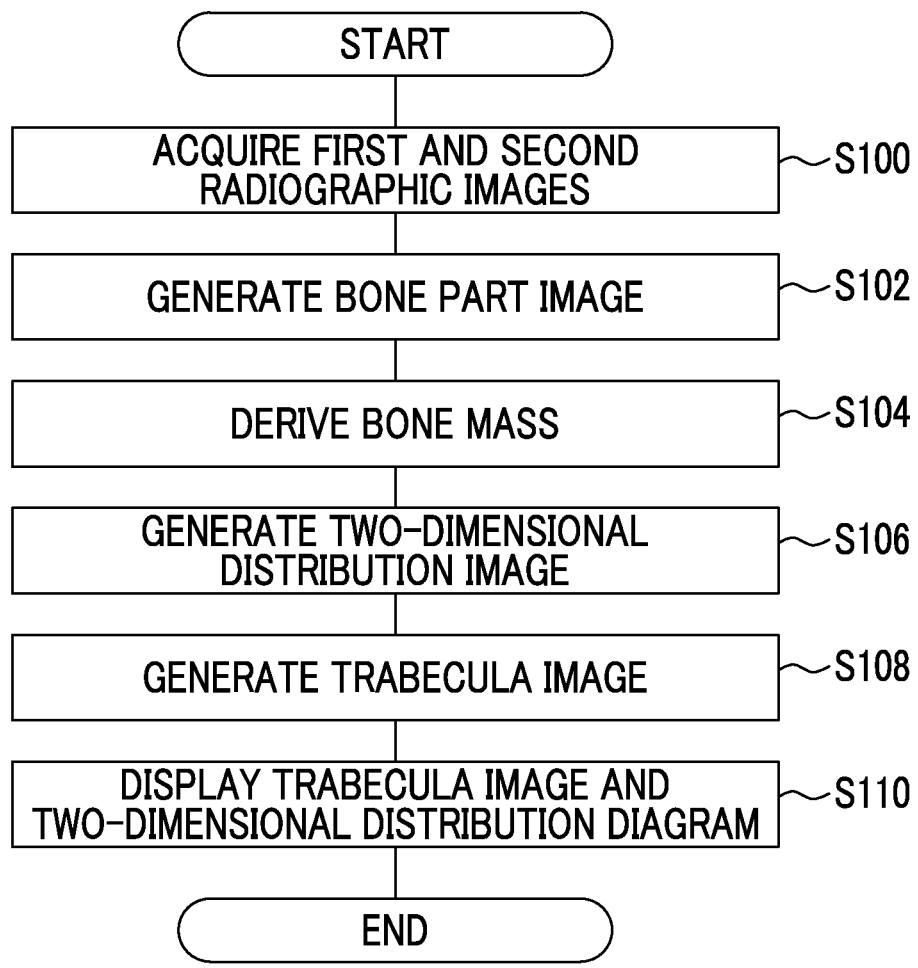
FIG. 10 is a flowchart showing an example of a flow of image processing that is executed by the image processing apparatus of the first embodiment.

Next, the operation of the image processing apparatus 10 of the embodiment will be described. FIG. 10 is a flowchart showing an example of a flow of image processing that is executed by the CPU 20 executing the image processing program 30. The image processing program 30 is executed, for example, in a case where an instruction to start execution is input by the user through the input unit 26.

In Step S100 shown in FIG. 10, as described above, the first acquisition unit 40 acquires the first radiographic image G1 and the second radiographic image G2 obtained by imaging the subject W from the first radiation detector 5 and the second radiation detector 6 of the radiography system 1, respectively.

In next Step S102, as described above, the bone part image generation unit 42 performs weighting subtraction shown in Expression (1) described above between the corresponding pixels in the first radiographic image G1 and the second radiographic image G2, thereby generating the bone part image Gb representing the bone part region with the bone tissue of the subject W.

In next Step S104, as described above, the derivation unit 44 derives the bone mass B of each pixel of the bone part image Gb by multiplying each pixel of the bone part region in the bone part image Gb by the correction coefficient C0 shown in Expression (2) described above.

In next Step S106, as described above, the distribution diagram generation unit 46 generates the two-dimensional distribution diagram Gd based on the bone mass B derived in Step S104.

In next Step S108, as described above, the trabecula image generation unit 50 pastes the medical image according to the bone mass, which is represented by the medical image information 36 acquired by the second acquisition unit 48, to each stage region in the bone part region of the first radiographic image G1 based on the two-dimensional distribution diagram Gd generated in Step S106 to generate the trabecula image Gt.

In next Step S110, the display controller 52 makes the display unit 24 display the two-dimensional distribution diagram Gd generated in Step S106 and the trabecula image Gt generated in Step S108. The display unit 24 may be made to also display the bone mass B derived in Step S104. In a case where the processing of Step S110 ends, the present image processing ends.

In this way, the image processing apparatus 10 of the embodiment generates the bone part image Gb from the first radiographic image G1 and the second radiographic image G2, and derives the bone mass B for each pixel of the bone part image Gb. Furthermore, the image processing apparatus 10 generates the two-dimensional distribution diagram Gd based on the derived bone mass B and pastes the medical image according to the bone mass B to the bone part region of the first radiographic image G1 based on the generated two-dimensional distribution diagram Gd to generate the trabecula image Gt representing the bone mass B of the bone tissue of the subject W.

With this, with the image processing apparatus 10 of the embodiment, since it is possible to provide the trabecula image Gt according to the bone mass B of the subject W to the subject W, it is possible to enable easy awareness of a decreased state of the bone mass B of the subject. Furthermore, with the image processing apparatus 10 of the embodiment, since it is possible to paste the medical image according to the bone mass B to the first radiographic image G1 to generate the trabecula image Gt, it is possible to easily generate the trabecula image Gt.

In addition, with the image processing apparatus 10 of the embodiment, since the two-dimensional distribution diagram Gd according to the bone mass B is generated and the display unit 24 is made to display the two-dimensional distribution diagram Gd, it is possible to enable easy confirmation of the distribution of the two-dimensional distribution diagram Gd.

In the embodiment, although the trabecula image Gt is generated by pasting the medical image to the first radiographic image G1, a radiographic image to which the medical image is pasted is not limited to the first radiographic image G1. For example, the medical image may be pasted to the second radiographic image G2 to generate the trabecula image Gt or, for example, the medical image may be pasted to the bone part image Gb to generate the trabecula image Gt.

Second Embodiment

Hereinafter, a second embodiment will be described in detail.

Figure 11:
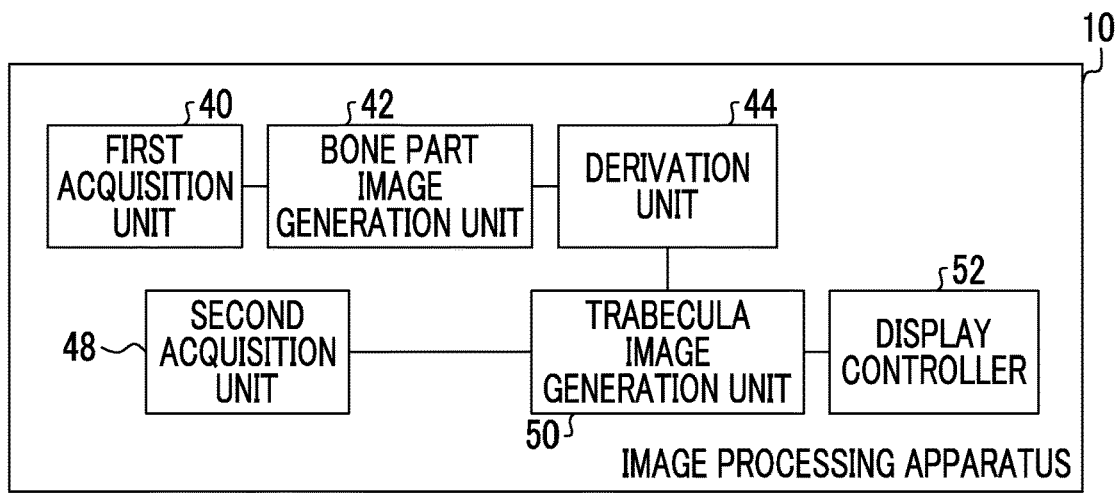
FIG. 11 is a functional block diagram showing an example of the functional configuration of an image processing apparatus of a second embodiment.

The hardware configuration of an image processing apparatus 10 of the embodiment is the same as the image processing apparatus 10 (see FIG. 2) of the first embodiment, and thus, description will not be repeated. FIG. 11 is a functional block diagram showing an example of the functional configuration of the image processing apparatus 10 of the embodiment. The image processing apparatus 10 of the embodiment is different from the image processing apparatus 10 (see FIG. 3) of the first embodiment in that the image processing apparatus 10 does not comprise the distribution diagram generation unit 46.

Figure 12:
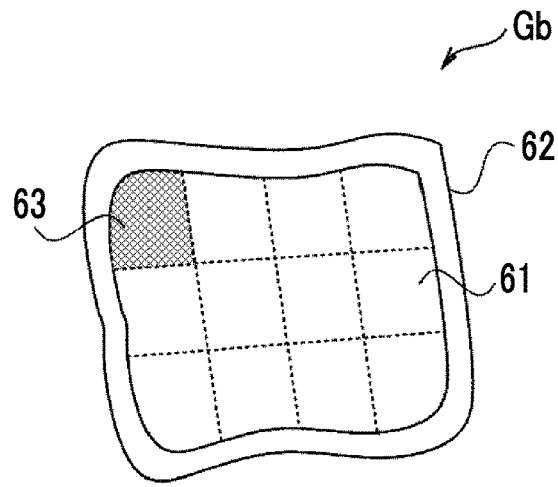
FIG. 12 is a diagram illustrating an example of derivation of a bone mass of each divided region with a derivation unit of the second embodiment.

Furthermore, in the image processing apparatus 10 of the embodiment, a way of deriving the bone mass B in the derivation unit 44 is different from the first embodiment. The derivation unit 44 of the embodiment derives a bone mass for each of a plurality of regions obtained by dividing a bone part region of the bone part image Gb. FIG. 12 shows a division example of a bone part region. In the division example shown in FIG. 12, a case where a region having a spongy structure in a bone part region corresponding to each of the first to fifth lumbar vertebrae is divided into a predetermined number (in FIG. 12, 12) of divided regions 63 is shown. In FIG. 12, for simplification, only a division example of a bone part image Gb corresponding to the third lumbar vertebra 62 (also see FIG. 7) is shown, and the divided regions 63 are indicated by dotted lines. A hatched region in FIG. 12 indicates one divided region 63 among the 12 divided regions 63.

In the embodiment, although a form has been made in which the number of divisions of the bone part region, that is, the number of divided regions 63 is predetermined, the number of divided regions 63 may be determined according to the type of the bone of the bone part region. For example, the number of divided regions 63 may be determined for each of the lumbar vertebrae and the thighbone. Alternatively, for example, the area of the divided region 63, instead of the number of divided regions 63, may be predetermined.

A method in which the derivation unit 44 derives the bone mass B of the divided region 63 is not particularly limited. For example, a form may be made in which the derivation unit 44 derives the bone mass B by multiplying each pixel of the divided region 63 by the correction coefficient C0 shown in Expression (2) described above and derives an average value of the derived bone masses B as the bone mass B of the divided region 63. Alternatively, for example, a form may be made in which the derivation unit 44 derives the bone mass b of each pixel of the divided region 63 as described above and derives a median value of the derived bone masses B as the bone mass B of the divided region 63.

Figure 13:
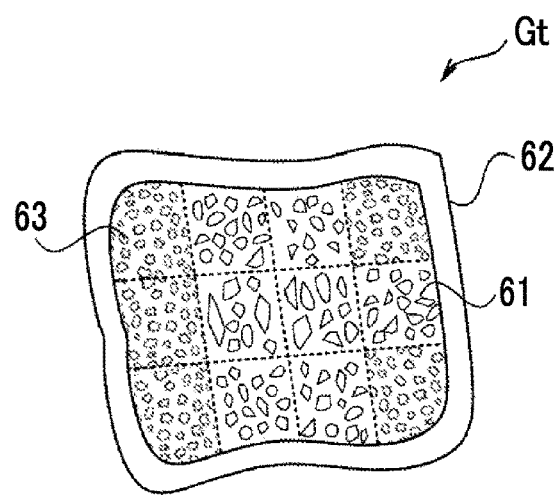
FIG. 13 is a diagram showing an example of a trabecula image that is generated by a trabecula image generation unit of the second embodiment.

In addition, in the image processing apparatus 10 of the embodiment, a way of generating the trabecula image Gt in the trabecula image generation unit 50 is different from the first embodiment. The trabecula image generation unit 50 of the embodiment pastes the medical image according to the bone mass B of the divided region 63 to each region of the first radiographic image G1 corresponding to the divided region 63, thereby generating the trabecula image Gt representing the trabecula of the bone tissue. FIG. 13 shows an example of the trabecula image Gt generated by the trabecula image generation unit 50 of the embodiment. In FIG. 13, for simplification, only the trabecula image Gt corresponding to the third lumbar vertebra 62 (see FIG. 12) is shown. Furthermore, in the trabecula image Gt shown in FIG. 13, dotted lines indicating the divided regions 63 are also displayed. In this way, the trabecula image Gt that is generated by the trabecula image generation unit 50 of the embodiment is composed of the medical image representing the trabecula according to the bone mass B for each divided region 63.

Figure 14:
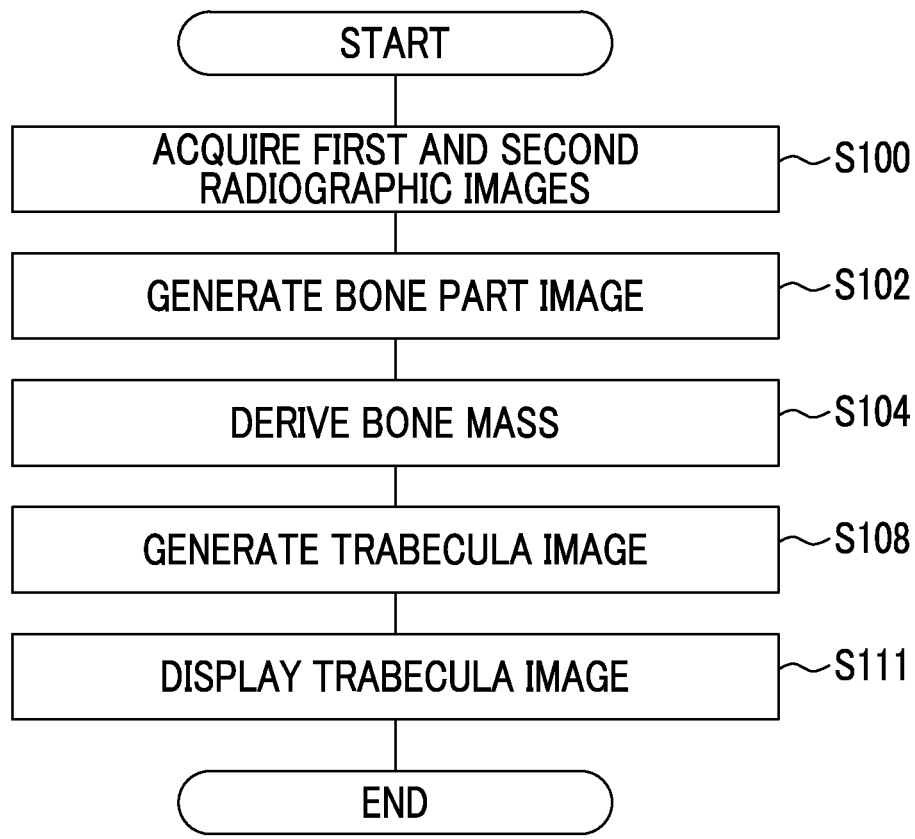
FIG. 14 is a flowchart showing an example of a flow of image processing that is executed by the image processing apparatus of the second embodiment.

Next, the operation of the image processing apparatus 10 of the embodiment will be described. FIG. 14 is a flowchart showing an example of a flow of image processing that is executed by the CPU 20 executing the image processing program 30. The image processing of the embodiment is different from the image processing (see FIG. 10) of the first embodiment in that the image processing does not include Step S106 and includes Step S111 instead of Step S110.

For this reason, in the image processing of the embodiment, in Step S104 shown in FIG. 14, as described above, the derivation unit 44 derives the bone mass B on all divided regions 63 by multiplying each pixel of each divided region 63 by the correction coefficient C0 shown in Expression (2) described above.

In next Step S108, as described above, the trabecula image generation unit 50 pastes the medical image according to the bone mass B of the divided region 63 derived in Step S104 to each region of the first radiographic image G1 corresponding to the divided region 63, thereby generating the trabecula image Gt representing the trabecula of the bone tissue.

In Step S111, the display controller 52 makes the display unit 24 display the trabecula image Gt generated in Step S108. In a case where the processing of Step S111 ends, the present image processing ends.

In this way, the image processing apparatus 10 of the embodiment derives the bone mass B for each divided region 63 obtained by dividing the bone part region and pastes the medical image according to the bone mass B to the region of the first radiographic image G1 corresponding to the divided region 63 based on the derived bone mass B to generate the trabecula image Gt representing the bone mass of the bone tissue of the subject W.

With this, even in the image processing apparatus 10 of the embodiment, since it is possible to provide the trabecula image Gt according to the bone mass B of the subject W to the subject W, it is possible to enable easy awareness of a decreased state of the bone mass of the subject. Furthermore, even in the image processing apparatus 10 of the embodiment, since it is possible to paste the medical image according to the bone mass B to the first radiographic image G1 to generate the trabecula image Gt, it is possible to easily generate the trabecula image Gt.

Third Embodiment

Hereinafter, a third embodiment will be described in detail.

Figure 15:
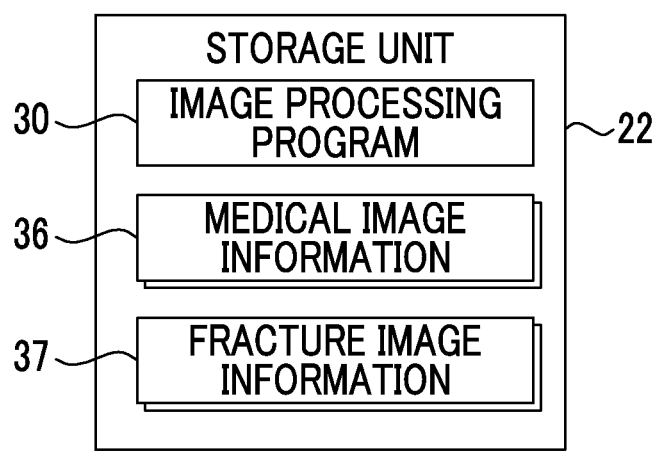
FIG. 15 is a diagram showing an example of a storage unit of the second embodiment.

The hardware configuration of an image processing apparatus 10 of the embodiment is the same as that of the image processing apparatus 10 (see FIG. 2) of the first embodiment excluding a part of information that is stored in the storage unit 22. As shown in FIG. 15, fracture image information 37 is further stored in the storage unit 22 of the image processing apparatus 10 of the embodiment.

Figure 16A:
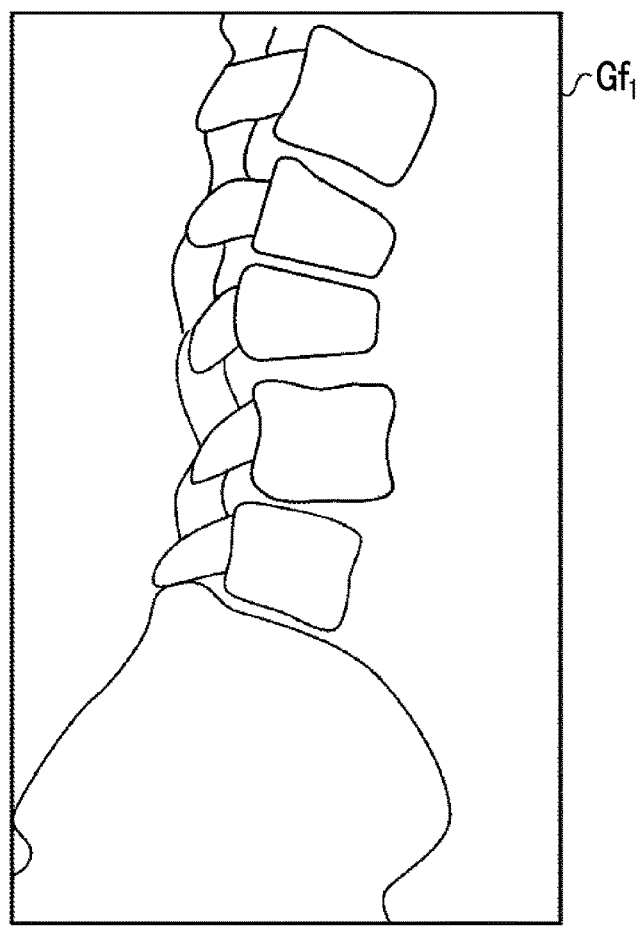
FIG. 16A is a diagram showing an example of a fracture image that is a radiographic image, in which a bone in a fractured state is targeted for imaging.
Figure 16B:
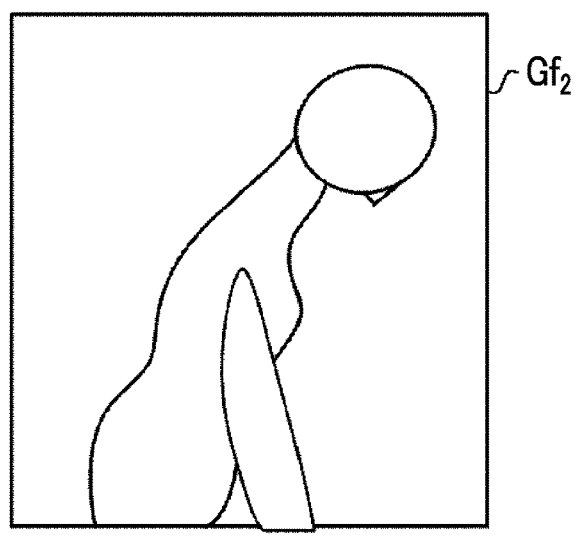
FIG. 16B is a diagram showing an example of a fracture image that is an optical photographic image, in which a person having a bone in a fractured state is captured.

As shown in FIGS. 16A and 16B, the fracture image information 37 is image information that represents an image representing a fractured state. FIG. 16A shows an example of a fracture image $Gf_1$ that is a radiographic image, in which a bone in a fractured state is targeted for imaging. In the fracture image $Gf_1$ shown in FIG. 16A, a state in which second and third lumbar vertebras have a compression fracture is captured. FIG. 16B shows an example of a fracture image $Gf_2$ that is an optical photographic image, in which a person having a bone in a fractured state is captured. In the fracture image $Gf_2$ shown in FIG. 16B, a person whose back is bowed due to the compression fracture of the second and third lumbar vertebrae is captured. In the embodiment, in the fracture image information 37, an image for which a person other than the subject W is a subject is used.

In the storage unit 22, a plurality of such fracture images Gf are stored in association with bone masses of bones in a fractured state that are targeted for imaging. A fracture image Gf of the embodiment is an example of an image in a case where a health problem of the present disclosure occurs.

Figure 17:
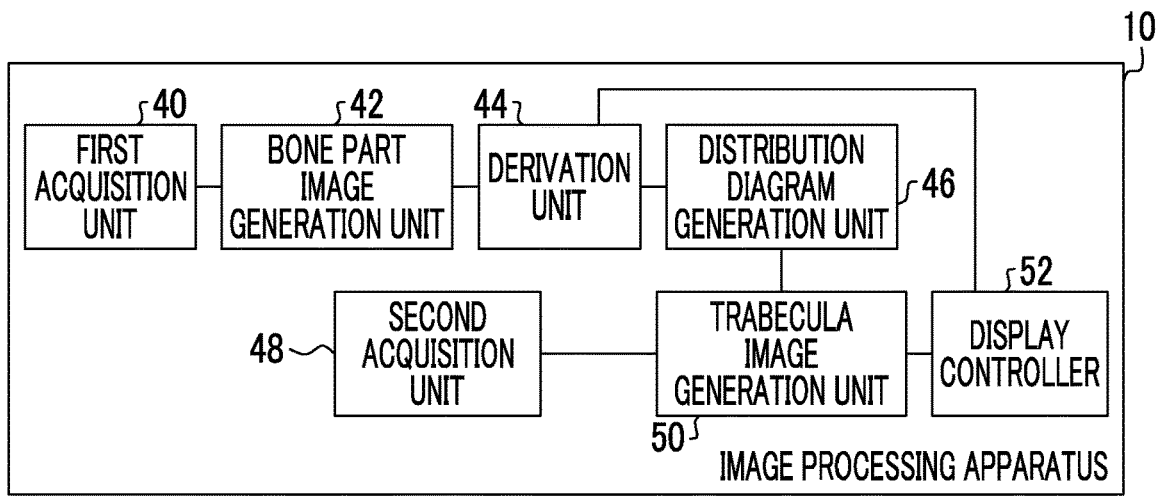
FIG. 17 is a functional block diagram showing an example of the functional configuration of an image processing apparatus of a third embodiment.

FIG. 17 is a functional block diagram showing an example of the functional configuration of the image processing apparatus 10 of the embodiment. The image processing apparatus 10 of the embodiment is the same as that of the image processing apparatus 10 (see FIG. 3) of the first embodiment excluding the configuration relating to the display controller 52.

The display controller 52 performs control such that the display unit 24 displays the trabecula image Gt generated by the trabecula image generation unit 50 as in the first embodiment, and the display unit 24 displays the fracture image Gf. Specifically, the display controller 52 acquires the fracture image Gf corresponding to the bone mass B obtained by subtracting a predetermined value from the bone mass B derived by the derivation unit 44 from the storage unit 22 and makes the display unit 24 display the acquired fracture image Gf. In acquiring the fracture image Gf, the predetermined value that is subtracted from the bone mass B derived from the derivation unit 44 is not particularly limited. For example, the value of the bone mass that decreases for six months from the current age may be applied as the predetermined value based on a predicted value of a decrease in bone mass due to aging.

In the display controller 52 of the embodiment, although a form has been made in which control is performed such that the fracture image Gf according to the bone mass B smaller than the current bone mass B of the subject W by the predetermined mass is displayed, the present disclosure is not limited to this form, and a form may be made in which control is performed such that the fracture image Gf according to the current bone mass B of the subject W is displayed.

Figure 18:
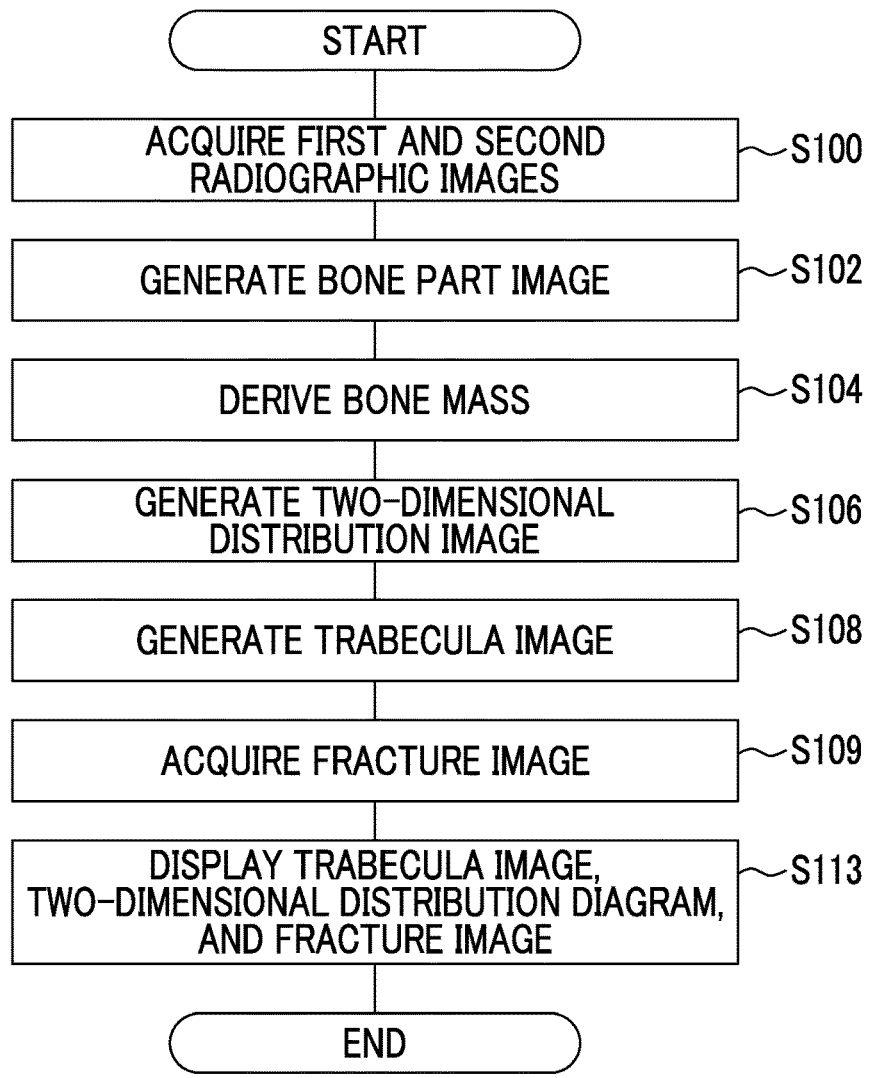
FIG. 18 is a flowchart showing an example of a flow of image processing that is executed by the image processing apparatus of the third embodiment.

Next, the operation of the image processing apparatus 10 of the embodiment will be described. FIG. 18 is a flowchart showing an example of a flow of image processing that is executed by the CPU 20 executing the image processing program 30. The image processing of the embodiment is different from the image processing (see FIG. 10) of the first embodiment in that the image processing includes Steps S109 and S113 instead of Step S110.

In the image processing shown in FIG. 18, in Step S109 next to Step S108, the display controller 52 acquires the fracture image information 37 representing the fracture image Gf according to the bone mass B smaller than the bone mass B derived by the derivation unit 44 by the predetermined mass from the storage unit 22 as described above.

In next Step S113, the display controller 52 makes the display unit 24 display the two-dimensional distribution diagram Gd generated in Step S106, the trabecula image Gt generated in Step S108, and the fracture image Gf acquired in Step S109. In a case where the processing of Step S113 ends, the present image processing ends.

In this way, the image processing apparatus 10 makes the display unit 24 further display the fracture image Gf according to the bone mass B smaller than the current bone mass B of the subject W by the predetermined amount or the fracture image Gf according to the current bone mass B of the subject W.

With this, with the image processing apparatus 10 of the embodiment, since it is possible to visually report a health problem that occurs in a case where the bone mass B decreases, it is possible to make the subject W become easily aware of the decrease in bone mass B.

In regard to the display controller 52, a form may be made in which, in a case where the bone mass B derived by the derivation unit 44 is equal to or greater than a predetermined bone mass, the fracture image Gf is not displayed. For example, a form may be made in which, in a case where the bone mass B derived by the derivation unit 44 is the bone mass B having little possibility that a health problem, such as a fracture, occurs due to a decrease in bone mass B within a predetermined period from the present, such as within six months from the present, the fracture image Gf is not displayed. As a specific example, a form may be made in which, in a case where a Young Adult Mean (YAM) value by the bone mass B derived by the derivation unit 44 is equal to or greater than 90%, the display controller 52 does not perform the acquisition and display of the fracture image Gf.

As described above, the image processing apparatus 10 of each embodiment described above comprises the first acquisition unit 40, the derivation unit 44, the second acquisition unit 48, and the trabecula image generation unit 50. The first acquisition unit 40 acquires the first radiographic image G1 and the second radiographic image G2 by simple imaging of the subject W including the bone tissue. The derivation unit 44 derives the bone mass B in the bone part region of the subject W based on the first radiographic image G1 and the second radiographic image G2. The second acquisition unit 48 acquires the medical image that represents the state of the trabecula and is different from the first radiographic image G1 and the second radiographic image G2. The trabecula image generation unit 50 applies the medical image to the bone part region of the first radiographic image G1 based on the bone mass B derived by the derivation unit 44 to generate the trabecula image Gt representing the trabecula of the bone tissue.

In this way, the image processing apparatus 10 of each embodiment described above generates the bone part image Gb from the first radiographic image G1 and the second radiographic image G2, derives the bone mass B of the bone part image Gb, and applies the medical image according to the bone mass B to the bone part region of the radiographic image of the first radiographic image G1 or the like based on the derived bone mass B to generate the trabecula image Gt representing the bone mass of the bone tissue of the subject W. With this, with the image processing apparatus 10 of each embodiment described above, since it is possible to provide the trabecula image Gt according to the current bone mass B of the subject W to the subject W, it is possible to enable easy awareness of a decreased state of the bone mass of the subject.

Furthermore, in the image processing apparatus 10 of each embodiment described above, since it is possible to paste the medical image according to the bone mass B to the radiographic image as an example of a form of applying the medical image according to the bone mass B to the bone part region of the radiographic image to generate the trabecula image Gt, it is possible to easily generate the trabecula image Gt.

Accordingly, with the image processing apparatus 10 of each embodiment described above, it is possible to easily generate the trabecula image Gt for enabling easy awareness of a decreased state of the bone mass B of the subject W. Furthermore, with the image processing apparatus 10, awareness of the decreased state of the bone mass B is provided, whereby it is possible to improve a motivation to prevention, early treatment, continuous treatment, and the like of osteoporosis or the like.

In addition, with the image processing apparatus 10 of each embodiment described above, since it is possible to use a radiographic image (first radiographic image G1 and second radiographic image G2) obtained by simple imaging instead of a Computed Tomography (CT) image, a Magnetic Resonance Imaging (MRI) image, or the like, it is possible to enable easy awareness of a decrease in the bone mass B of the subject W with a simpler apparatus.

The present disclosure is not limited to the respective embodiments described above, and a form may be made in which the image processing apparatus 10 further generates another image for providing awareness of a current state of the bone mass B of the subject W, makes the display unit 24 display the image, and the like. For example, a form may be made in which the display unit 24 is made to display a bone strength distribution image according to the bone mass B derived by the derivation unit 44. A method in which the image processing apparatus 10 derives bone strength is not particularly limited, and for example, a method using the density of a trabecula structure (spongy structure) is exemplified. In this method, first, the image processing apparatus 10 extracts a high-frequency component of an image of the bone part region in the bone part image Gb using any method, such as Fourier transform, wavelet transform, or a method using a high-pass filter. Then, the image processing apparatus 10 calculates a variance value of the high-frequency components for each pixel of the bone part region. Here, as the density of the trabecula structure is lower, the calculated variance value of the high-frequency components becomes smaller. For this reason, the image processing apparatus 10 calculates bone strength by an arithmetic operation of the bone mass B×the variance value. Here, since the bone mass and the variance value are acquired for each pixel in the bone part region, the bone strength is also calculated for each pixel.

In the respective embodiments described above, although a form is made in which the trabecula image Gt is generated using the bone mass B derived by the derivation unit 44, a value corresponding to the bone mass B, such as the YAM value, is used instead of the bone mass B.

In the respective embodiments described above, in generating the trabecula image Gt, as an example of a form in which the medical image is applied to the bone part region of the radiographic image, a form in which the medical image according to the bone mass B is pasted to the bone part region of the radiographic image has been described; however, the present disclosure is not limited to this form. For example, a form may be made in which the medical image is applied to a portion of the bone part region of the radiographic image to generate the trabecula image Gt. As this form example, a form in which the trabecula image Gt is generated by applying the medical image to a portion in the bone part region having the bone mass B equal to or less than a predetermined threshold value and keeping a portion having the bone mass B exceeding the predetermined threshold value as an original image (radiographic image) is exemplified. In this form example, the trabecula image Gt is an image in which the medical image and the original image are mixed, and since a portion where the bone mass B is low is replaced with the medical image, a portion where the bone mass B decreases is easily recognized. Alternatively, for example, a form may be made in which the trabecula image Gt is generated by replacing the entire image of the bone part region of the radiographic image with the medical image. As this form example, a form in which the trabecula image Gt is generated by applying the medical image to a lumbar vertebra having the bone mass B equal to or less than the predetermined threshold value among a plurality of lumbar vertebrae included in the bone part region and keeping a lumbar vertebra having the bone mass B exceeding the predetermined threshold value among a plurality of lumbar vertebrae as an original image (radiographic image) is exemplified. In a case of this form example, since the trabecula image Gt is an image in which a medical image and an original image are mixed or an image representing a bone having a low bone mass B is replaced with the medical image, a bone where the bone mass B decreases is easily recognized.

Furthermore, an image that is used in deriving a bone mass in the respective embodiments described above may be a reduced image. For example, the derivation unit 44 may derive a bone mass for each pixel of a reduced image obtained by reducing the bone part image Gb. In a case where a reduced image is used in this way, since it is possible to reduce noise to improve a Signal to Noise ratio (SN ratio), it is possible to improve derivation accuracy.

In the respective embodiments described above, although the first radiographic image G1 and the second radiographic image G2 are acquired by a one-shot method, the first radiographic image G1 and the second radiographic image G2 may be acquired by a so-called two-shot method in which imaging is performed two times. In this case, the radiography system 1 may comprise one radiation detector. As the imaging conditions, any of the imaging conditions when the first radiographic image G1 is acquired and the imaging conditions when the second radiographic image G2 is acquired may be used. In a case of a two-shot method, there is a possibility that the position of the subject W included in the first radiographic image G1 and the second radiographic image G2 is deviated due to body movement of the subject W during imaging. For this reason, it is preferable that the processing of each embodiment described above is executed after registration of the subject W is performed in the first radiographic image G1 and the second radiographic image G2. As processing of registration, for example, a method described in JP2011-255060A can be used. The method described in JP2011-255060A generates a plurality of first range images and a plurality of second range images representing structures having different frequency ranges for the first radiographic image G1 and the second radiographic image G2, respectively, acquires a position deviation amount between corresponding positions in the first range image and the second range image with the corresponding frequency range, and registers the first radiographic image G1 and the second radiographic image G2 based on the position deviation amount.

As the hardware structures of processing units that execute various kinds of processing, such as the functional units of the image processing apparatus 10 in the above-described embodiments, various processors described below can be used. Various processors include a programmable logic device (PLD) that is a processor capable of changing a circuit configuration after manufacture, such as a field programmable gate array (FPGA), a dedicated electric circuit that is a processor having a circuit configuration dedicatedly designed for executing specific processing, such as an application specific integrated circuit (ASIC), and the like, in addition to a CPU that is a general-purpose processor executing software (program) to function as various processing units, as described above.

One processing unit may be configured of one of various processors described above or may be configured of a combination of two or more processors (for example, a combination of a plurality of FPGAs or a combination of a CPU and an FPGA) of the same type or different types. A plurality of processing units may be configured of one processor.

As an example where a plurality of processing units are configured of one processor, first, as represented by a computer, such as a client or a server, there is a form in which one processor is configured of a combination of one or more CPUs and software, and the processor functions as a plurality of processing units. Secondly, as represented by system on chip (SoC) or the like, there is a form in which a processor that realizes all functions of a system including a plurality of processing units into one integrated circuit (IC) chip is used. In this way, various processing units may be configured using one or more processors among various processors described above as a hardware structure.

In addition, the hardware structure of various processors is, more specifically, an electric circuit (circuitry), in which circuit elements, such as semiconductor elements, are combined.

In the above-described embodiments, although a form in which the image processing program 30 is stored (installed) in advance in the storage unit 22 has been described, the present disclosure is not limited thereto. The image processing program 30 may be provided in a form of being recorded in a recording medium, such as a compact disc read only memory (CD-ROM), a digital versatile disc read only memory (DVD-ROM), and a universal serial bus (USB). Alternatively, a form may be made in which the image processing program 30 is downloaded from an external apparatus through a network.

From the above description, it is possible to ascertain the technique related to the following supplementary item.

Supplementary Item

An image processing apparatus comprising:
a processor; and
a memory incorporated in or connected to the processor,
in which the processor is configured to
acquire a radiographic image obtained by simple imaging of a subject including a bone tissue,
derive a bone mass in a bone part region of the subject based on the radiographic image,
acquire a medical image, which represents a state of a trabecula and is different from the radiographic image, and
apply the medical image to the bone part region of the radiographic image based on the derived bone mass to generate a trabecula image representing a trabecula of the bone tissue.

What is claimed is:
1. An image processing apparatus comprising at least one processor,
the at least one processor being configured to:
acquire a two-dimensional radiographic image of a subject including a bone tissue;
derive a bone mass in a bone part region of the subject based on the two-dimensional radiographic image;
acquire a plurality of two-dimensional medical images, each of which represents a state of a trabecula and is different from the two-dimensional radiographic image; and based on the bone mass that has been derived, subdivide the bone part region of the two-dimensional radiographic image into a plurality of stage regions associated with a plurality of stages of the bone mass, and for each of the plurality of stage regions, select, from the plurality of two-dimensional medical images, a two-dimensional medical image representing the state of the trabecula corresponding to the stage of the bone mass associated with each of the plurality of stage regions, and apply the selected two-dimensional medical image to each of the plurality of stage regions to generate a two-dimensional trabecula image representing a trabecula of the bone tissue.

2. The image processing apparatus according to claim 1, wherein the plurality of two-dimensional medical images is a plurality of two-dimensional medical images captured by an imaging apparatus for imaging the state of a trabecula of a bone.

3. The image processing apparatus according to claim 1, wherein the at least one processor is configured to paste the plurality of two-dimensional medical images to the bone part region of the two-dimensional radiographic image to generate the two-dimensional trabecula image representing the trabecula of the bone tissue.

4. The image processing apparatus according to claim 3, wherein the at least one processor is configured to:
derive a bone mass for each pixel of the bone part region, and
paste the plurality of two-dimensional medical images to each pixel of the bone part region to generate the two-dimensional trabecula image.

5. The image processing apparatus according to claim 1, wherein the at least one processor is configured to:
generate a distribution diagram of the bone mass in the bone part region based on the bone mass that has been derived, and
generate the two-dimensional trabecula image based on the distribution diagram.

6. The image processing apparatus according to claim 1, wherein the at least one processor is configured to:
acquire a first radiographic image and a second radiographic image acquired by radiation having different energy distributions transmitted through the subject as the two-dimensional radiographic image,
generate a bone part image representing the bone part region with a bone tissue of the subject from the first radiographic image and the second radiographic image,
derive the bone mass based on the bone part image, and
apply the plurality of two-dimensional medical images to the bone part region of any one of the first radiographic image, the second radiographic image, and the bone part image to generate the two-dimensional trabecula image.

7. The image processing apparatus according to claim 1, further comprising:
a display controller that makes a display unit display an image in a case where a health problem occurs in the bone mass that has been derived or a bone mass smaller than the bone mass that has been derived by a predetermined mass.

8. An image processing method comprising:
acquiring a two-dimensional radiographic image of a subject including a bone tissue;
deriving a bone mass in a bone part region of the subject based on the two-dimensional radiographic image;
acquiring a plurality of two-dimensional medical images, each of which represents a state of a trabecula and is different from the two-dimensional radiographic image; and
based on the bone mass that has been derived, subdividing the bone part region of the two-dimensional radiographic image into a plurality of stage regions associated with a plurality of stages of the bone mass, and for each of the plurality of stage regions, select, from the plurality of two-dimensional medical images, a two-dimensional medical image representing the state of the trabecula corresponding to the stage of the bone mass associated with each of the plurality of stage regions, and apply the selected two-dimensional medical image to each of the plurality of stage regions to generate a two-dimensional trabecula image representing a trabecula of the bone tissue.

9. A non-transitory computer-readable storage medium storing therein an image processing program that causes a computer to execute:
acquiring a two-dimensional radiographic image of a subject including a bone tissue;
deriving a bone mass in a bone part region of the subject based on the two-dimensional radiographic image;
acquiring a plurality of two-dimensional medical images, each of which represents a state of a trabecula and is different from the two-dimensional radiographic image; and
based on the bone mass that has been derived, subdividing the bone part region of the two-dimensional radiographic image into a plurality of stage regions associated with a plurality of stages of the bone mass, and for each of the plurality of stage regions, select, from the plurality of two-dimensional medical images, a two-dimensional medical image representing the state of the trabecula corresponding to the stage of the bone mass associated with each of the plurality of stage regions, and apply the selected two-dimensional medical image to each of the plurality of stage regions to generate a two-dimensional trabecula image representing a trabecula of the bone tissue.

10. The image processing apparatus according to claim 1, wherein the at least one processor is configured to, for each of the plurality of stage regions, derive an average value of the bone mass associated with each of the plurality of stage regions, and apply the plurality of medical images representing the state of the trabecula corresponding to the bone mass that is equal to the average value that has been derived.

11. The image processing apparatus according to claim 1, wherein the plurality of stage regions are determined based on values of the bone mass in each respective stage region.

12. The image processing apparatus according to claim 1, wherein the plurality of stage regions are identified by different colors in the two-dimensional trabecula image.

13. The image processing apparatus according to claim 1, wherein the plurality of stage regions includes a predetermined number of stage regions.

14. The image processing apparatus according to claim 13, wherein the predetermined number of stage regions is based on a type of the bone part region.

15. The image processing apparatus according to claim 1, wherein each of the plurality of stage regions has a predetermined area.

16. The image processing apparatus according to claim 1, wherein each of the plurality of stage regions the stage regions are arranged concentrically within the bone part region.

17. The image processing apparatus according to claim 1, wherein each of the plurality of stage regions are arranged in a grid within the bone part region.

18. The image processing apparatus according to claim 1, wherein extents of each of the plurality of stage regions are indicated with lines in the two-dimensional trabecula image.

19. The image processing apparatus according to claim 1, wherein
- a first stage region of the plurality of stage regions is associated with a first bone mass stage of the plurality of stages of the bone mass,
- a first state of the trabecula corresponds to the first bone mass stage,
- a second stage region of the plurality of stage regions is associated with a second bone mass stage of the plurality of stages of the bone mass,
- a second state of the trabecula corresponds to the second bone mass stage, and
- the first state of the trabecula is different than the second state of the trabecula.

\* \* \* \* \*